United States Patent
Brockhoff et al.

(12)

(10) Patent No.: US 6,312,414 B1
(45) Date of Patent: *Nov. 6, 2001

(54) BLOOD-GAS SEPARATION DEVICE

(76) Inventors: Alexander Brockhoff, Gebhardstorkel 10, FL-9494, Schaan, Furstentum (LI); Hans Plechinger, Cherry Creek Ranch, SS 3 Site 15-130 Cranbrook B.C. (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/934,908

(22) Filed: Sep. 22, 1997

(30) Foreign Application Priority Data

Dec. 5, 1996 (DE) .............................. 196 50 406

(51) Int. Cl.[7] ....................................... A61M 5/00
(52) U.S. Cl. .................. 604/264; 604/4; 604/35
(58) Field of Search .................. 604/264, 272, 604/280, 4–6, 19, 21, 28, 35

(56) References Cited

U.S. PATENT DOCUMENTS

| 2,876,860 | 3/1959 | Clark, et al. .............. 183/2.5 |
| 3,715,863 | 2/1973 | Zanoni . |
| 3,753,336 | 8/1973 | Drew et al. . |
| 3,771,290 | 11/1973 | Stethem . |
| 3,785,380 | 1/1974 | Brumfield .............. 128/276 |
| 3,807,401 | 4/1974 | Riggle, et al. .......... 128/277 |
| 3,812,655 | 5/1974 | Bennett . |
| 3,833,013 | 9/1974 | Leonard . |
| 3,912,468 | 10/1975 | Tsuchiya et al. . |
| 3,955,573 | 5/1976 | Hansen, et al. .......... 128/276 |
| 3,965,896 | 6/1976 | Swank . |
| 3,994,689 | 11/1976 | Dewall . |
| 3,996,027 | 12/1976 | Schnell et al. . |
| 4,053,291 | 10/1977 | Sims . |

(List continued on next page.)

FOREIGN PATENT DOCUMENTS

| 2261127 | 6/1973 | (DE) . |
| 26 11 383 | 9/1977 | (DE) . |
| 2621051 | 12/1977 | (DE) . |
| 3011681 | 10/1980 | (DE) . |
| 2063108 | 6/1981 | (DE) . |
| 3222345 | 1/1983 | (DE) . |
| 36 41 644 | 10/1987 | (DE) . |
| 3624363 | 1/1988 | (DE) . |
| 3448173 | 2/1989 | (DE) . |
| 3641644 | 5/1989 | (DE) . |
| 43 26 886 | 2/1995 | (DE) . |
| 4326886 | 2/1995 | (DE) . |
| 43 29 385 | 3/1995 | (DE) . |
| 4329385 | 3/1995 | (DE) . |
| 29500879 | 2/1996 | (DE) . |
| 195 45 404 | 6/1997 | (DE) . |
| 0 318 993 | 6/1989 | (EP) . |
| 0 778 031 | 12/1995 | (EP) . |
| 1526509 | 9/1978 | (GB) . |
| 92 20380 | 11/1992 | (WO) . |

*Primary Examiner*—John D. Yasko
(74) *Attorney, Agent, or Firm*—Beck & Tysver, P.L.L.C.

(57) ABSTRACT

A blood suction apparatus for aspirating blood from a patient is developed as a one-hand held instrument having a handgrip. A centrifuge chamber, shaped to narrow from its tangentially directed top blood inlet to its bottom blood outlet end, like a funnel. A gas outlet opening from a gas collection space above the chamber and to which a suction device can be connected. A blood outlet at the lower end of the centrifuge chamber with both outlets connectable to a source of suction. The orientations of the handgrip and of elements passing through the handgrip are disclosed.

15 Claims, 4 Drawing Sheets

U.S. PATENT DOCUMENTS

| | | |
|---|---|---|
| 4,054,522 | 10/1977 | Pinkerton . |
| 4,061,031 | 12/1977 | Grimsrud . |
| 4,093,428 | 6/1978 | Swogger . |
| 4,102,655 | 7/1978 | Jeffery et al. . |
| 4,247,309 | 1/1981 | Buddenhagen . |
| 4,282,016 | 8/1981 | Tauber et al. . |
| 4,316,271 | 2/1982 | Evert . |
| 4,344,777 | 8/1982 | Siposs . |
| 4,345,919 | 8/1982 | Wilkinson et al. . |
| 4,360,428 | 11/1982 | Comparetto et al. . |
| 4,368,118 | 1/1983 | Siposs . |
| 4,388,922 | 6/1983 | Telang . |
| 4,394,138 | 7/1983 | Schilling . |
| 4,433,971 | 2/1984 | Lindsay et al. . |
| 4,474,184 | 10/1984 | Harui . |
| 4,475,932 | 10/1984 | Hull et al. . |
| 4,547,186 | 10/1985 | Bartlett ................................ 604/4 |
| 4,555,253 | 11/1985 | Hull et al. . |
| 4,585,465 | 4/1986 | Suzuki et al. . |
| 4,690,762 | 9/1987 | Katsura . |
| 4,710,299 | 12/1987 | Prendergast, Gavan J.J. . |
| 4,749,387 | 6/1988 | Lotz . |
| 4,806,135 | 2/1989 | Siposs . |
| 4,860,591 | 8/1989 | Garland . |
| 4,874,359 | 10/1989 | White et al. . |
| 4,900,308 | 2/1990 | Verkaart . |
| 4,940,473 | 7/1990 | Benham . |
| 4,966,703 | 10/1990 | Kalnins et al. . |
| 5,061,236 | 10/1991 | Sutherland et al. . |
| 5,152,964 | 10/1992 | Leonard . |
| 5,188,604 | 2/1993 | Orth . |
| 5,228,889 | 7/1993 | Cortial et al. . |
| 5,386,734 * | 2/1995 | Pusinelli ............................. 604/4 X |
| 5,411,472 | 5/1995 | Steg Jr., et al. . |
| 5,429,595 | 7/1995 | Wright, Jr. et al. . |
| 5,451,321 | 9/1995 | Matkovich ......................... 210/641 |
| 5,486,162 | 1/1996 | Brumbach . |
| 5,503,801 | 4/1996 | Brugger . |
| 5,531,119 | 7/1996 | Meyers . |
| 5,537,335 | 7/1996 | Antaki et al. . |
| 5,582,633 | 12/1996 | Jiang et al. . |
| 5,591,251 | 1/1997 | Brugger . |
| 5,632,894 | 5/1997 | White et al. . |
| 5,674,199 | 10/1997 | Brugger . |
| 5,707,431 | 1/1998 | Verkaart et al. . |
| 5,755,965 | 5/1998 | Reiber . |

* cited by examiner

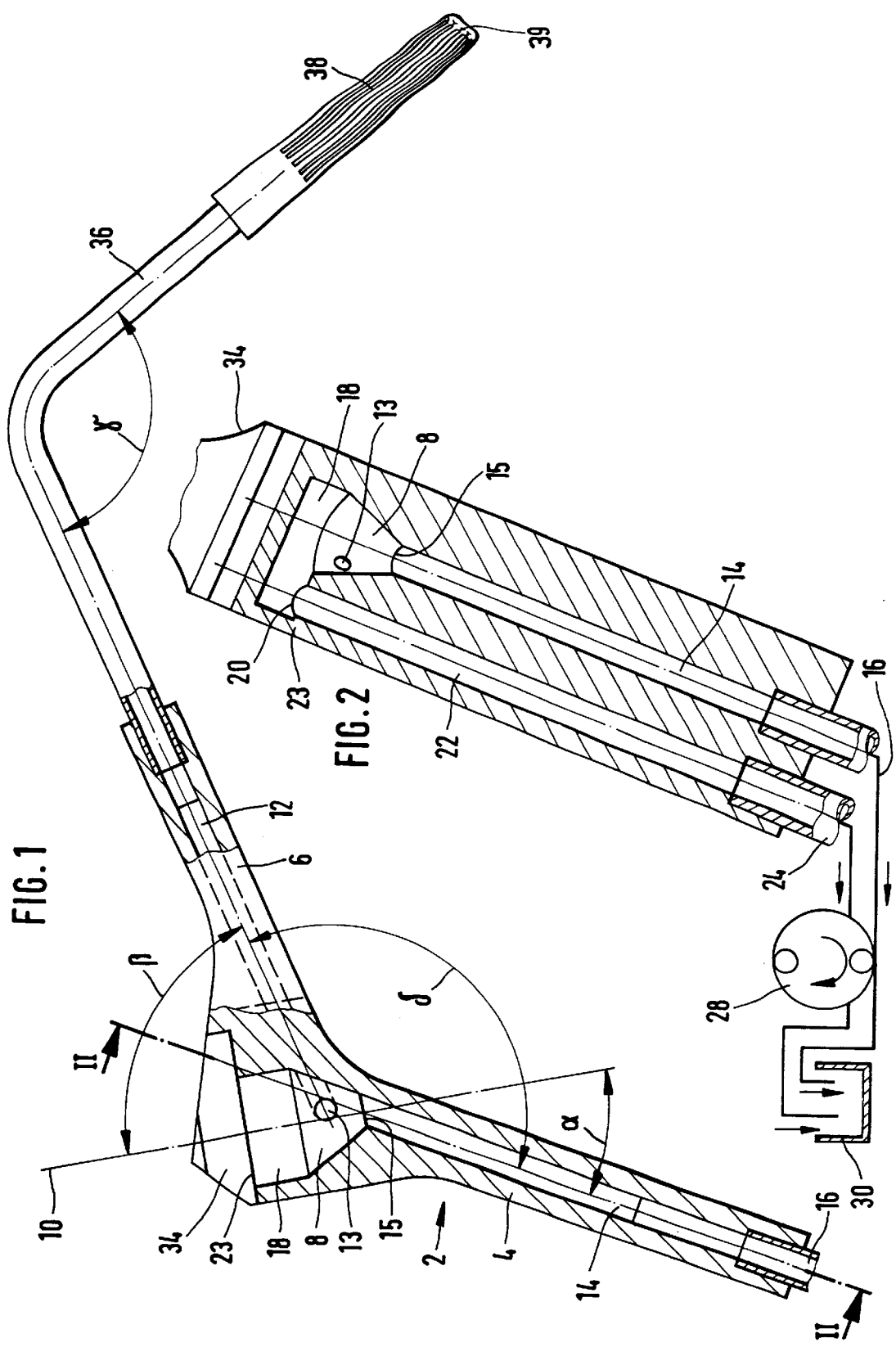

BLOOD-GAS SEPARATION DEVICE

BACKGROUND OF THE INVENTION

The present invention relates to an apparatus for suctioning blood and for separating blood and gas and particularly to moving blood through a non-rotating centrifuge for separating blood and gas.

When blood is drawn from a patient, in particular from the site of a wound which may result from a surgical operation or an accident, and this blood is then to be used again for the same patient or for another patient, the blood must be again separated as soon as possible, and as close as possible to the place of removal from the patient, from the air which may have been drawn into the blood at the place where it was drawn is from the patient. Blood which contains air must under no circumstances be administered to a patient. Furthermore, blood is damaged by inclusions of air the longer air which has been drawn-in remains in the blood, and the more the air is mixed with this blood over the blood-removal path.

The quality of blood can be impaired among other things by the amount and length of presence of air or other gases in the blood; by suction or pressure forces on the blood; by frictional forces of the blood in flow paths, and by deflections of the flow of blood and turbulence in the blood.

Upon the degassing of blood, a distinction must be made between different uses, since they have different purposes and different conditions.

In a first case of use, blood is degasified while it is drawn in relatively small and strongly varying amounts from a patient, in particular through a suction tube from the site of a wound which may have been caused by an accident or an operation. Vacuum for drawing the blood is produced by a suction pump, generally a roller pump. The suction pump not only draws off blood but frequently also draws off air at the place where blood is being removed from the patient. The amount of air which is drawn off is relatively large, as compared with the amount of blood being drawn off, for instance five parts of air to one part of blood (parts by volume). The blood-removal rate is relatively low, for example 100 to 600 milliliters per minute, and it varies greatly. The suction flow speed of the blood is also relatively low and varies greatly.

The air bubbles contained in the blood are frequently relatively large. Their size ranges from the micrometer range to the millimeter range. The present invention concerns this field of use, namely degasifying blood while it is being drawn off from a patient.

The second case of use concerns administering blood to a patient, for instance upon dialysis or after a large loss of blood in an accident. Blood which is administered to a patient cannot be fed by suction but can only be administered to the patient by the pressure of a pressure pump. The blood rate, for instance three liters per minute, and the speed of conveyance of the blood are relatively high and substantially constant. The amount of air in the blood is, however, slight, for instance only $50 \times 10^{-6}$ parts by volume of air to one part by volume of blood. The air has the form of only very small bubbles in the micrometer range.

The third case of use concerns the handling of blood outside a patient and independently of the patient. Here, similar to the second case, there are substantially constant blood flow quantities and constant speeds of flow of blood.

For the first case of use, U.S. Pat. No. 3,785,380 discloses a blood removal device which consists of a cylindrical housing in which microporous filter material is present for filtering air bubbles and other impurities out of a stream of blood drawn off from a patient, a blood suction tube at a front end of the housing, and a blood suction line at the rear end of the housing.

Literature concerning the second case of use includes GB-A-2 063 108 which shows a blood degasification device for removing bubbles of gas which can be so small as to lie in the micro range, for instance having a diameter of only 40 microns. This blood suction device has a vertically arranged cylindrical cyclone chamber, with a tangential inlet at the upper end of the chamber, and a blood outlet at the 49 lower end of the chamber arranged tangentially opposite the direction of rotation of the cyclone. An air vent tube extends in downward direction in the axis of rotation of the cyclone to a level below the blood inlet into the cyclone chamber. A second venting means is in the form of a radial hole in an upper extension of the cyclone chamber above the blood inlet. A second tube extends through the entire cyclone chamber along the axis of rotation of the cyclone and through a part of the first mentioned tube. The second tube serves so that air bubbles collect on its outer surface and can rise upward. German DE-A-43 29 385 describes an air separator which is an improvement on the one described in the above described GB-A-2 063 108. In the German publication, the blood inlet and blood outlet are arranged axially to each other at the ends of a cylindrical eddy chamber which face each other. The blood inlet is formed by a guide blade body and there is a filter candle in front of the blood outlet. Ascending bubbles of blood enter into a section of the eddy chamber which is located above the guide blade body and in which an air cushion is formed which is vented by a hole. German DE-C-36 41 644 shows a blood flow chamber having a blood inlet at the mid-height of the chamber and a blood outlet channel immersed in the flow chamber. Air bubbles contained in the blood can rise upward only due to the Archimedean buoyancy force.

Furthermore, German DE-C-36 24 363 and U.S. Pat. No. 5,451,321 show devices with microporous filter material for filtering gas bubbles or other blood impurities out of a stream of blood.

SUMMARY OF THE INVENTION

The object of the present invention is substantially to reduce the aforementioned impairments in the blood caused upon drawing blood from a patient. Another object is to do this by a low weight, inexpensive apparatus which is easy to operate.

This object is achieved with an apparatus having a non-rotating centrifuge chamber with a vertical axis and with a blood inlet above and a blood outlet below, wherein blood enters tangentially, flows around the chamber and exits the outlet. The apparatus is widened above the centrifuge chamber to produce an enlarged gas space wherein gas from the blood flow can separate and be drawn off through a gas outlet. The apparatus is developed and sized to be carried in one hand and includes a hand grip for that purpose. The blood inlet channel is connected at or is the rear end of the blood suction tube.

The centrifugal chamber is preferably funnel shaped, wide toward the upper end inlet and narrowing toward the lower end outlet. The blood inlet suction channel is angled at an angle, open at the top, of less than 90° to the axis of rotation. For compactness, various elements may be in or may run through the hand grip of the apparatus, those elements including the centrifuge chamber and various blood or gas flow channels.

The invention has following advantages: The blood suction apparatus can be arranged close to a patient. It is very light in weight. It can be produced at low cost by the use of commercial tubes. It is simple to handle and not fatiguing for the operator. The invention utilizes the centrifugal forces of a cyclone flow for the removal of gas bubbles of all sizes. The gas removal suction action is applied on the rotating blood from above, and the Archimedean buoyancy forces simultaneously and in a manner support each other, so that with even only a weak suction of a suction pump, gentle and at the same time effective separation of the gas phase from the blood phase takes place.

If, in accordance with the invention, the cyclone chamber has the shape of a funnel which becomes narrower from the blood inlet to the blood outlet, then the centrifugal kinetic energy of the cyclone flow is better maintained from the blood inlet to the blood outlet than in the case of a non-funnel-shaped cylindrical chamber. Even with small quantities of blood flow and low blood flow speeds rotation of the blood is still produced with sufficient centrifugal force to remove air from the blood, even in the case of weak suction of the suction pump. The effects and advantages of the funnel-shaped cyclone chamber are further improved if the blood inlet channel is directed not only approximately tangentially but also obliquely downward into the cyclone chamber. In this case, even small drop-like amounts of blood are rotated in the cyclone chamber by the suction of the blood suction pump and freed of air bubbles.

Better separation of blood and gas from the blood-gas suction stream is obtained, in accordance with a special idea of the invention, by a gas space above the rotating stream of blood. In that space, gas bubbles and blood-gas foam have sufficient time and space to break down into an air portion and a blood portion before the gas is drawn off at a distance above the rotating stream of blood by a gas suction device.

As used herein, "gas" is particularly air, but may be some other gaseous substance.

Other features and advantages of the present invention will become apparent from the following description of the invention which refers to the accompanying drawings.

BRIEF DESCRIPTION OF THE DRAWINGS

FIG. 1 is a side view, partially along the plane I—I of FIG. 3, of a blood suction device according to the invention;

FIG. 2 is a diagrammatic longitudinal section along the plane II—II of FIG. 1;

DETAILED DESCRIPTION OF THE INVENTION

Figure 3:
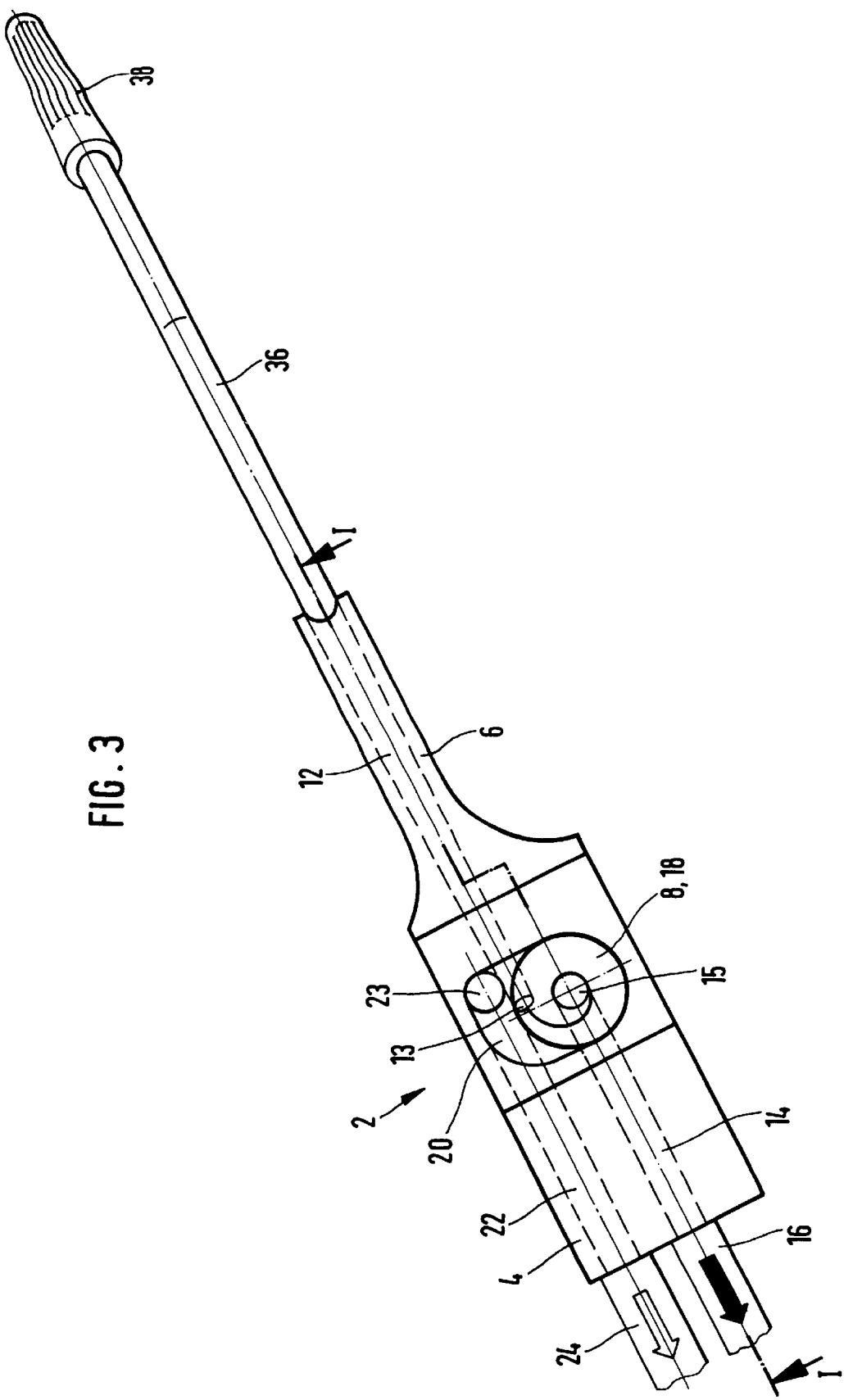
FIG. 3 is a top view of the blood suction device of FIG. 1.

The embodiment of a blood suction device of the invention for drawing blood from a patient, particularly from a wound site of a patient, which is shown in FIGS. 1 to 3, is a single hand held and operated device. It contains a single piece or multi-piece pistol shaped body 2 of metal or plastic which is comprised of a grip 4 and a barrel or shaft 6.

In the crossing region of the body 2, between grip 4 and shaft 6, there is a non-rotating centrifuge chamber, also referred to as a cyclone chamber 8, for producing a stream of blood which rotates in cyclone-like manner with constant direction of rotation around an upright, vertical or approximately vertical axis of rotation 10. The cyclone chamber 8 has a shape which narrows like a funnel downward from its top to its bottom so that a stream of blood drawn down through the chamber 8 substantially retains its kinetic energy throughout the entire cyclone chamber without a strong suction force being necessary in the cyclone chamber.

A blood inlet suction channel 12 in the shaft 6 debouches at a blood inlet opening 13 located approximately tangentially and obliquely downward at an angle β of 90°, or preferably less than 90°, to the vertical axis of rotation 10 and opens into the funnel shaped upper section of the funnel shaped cyclone chamber 8.

A blood outlet suction channel 14 extends from a blood outlet opening 15 at the narrow lower end of the cyclone chamber 8 at a downwardly open angle α of between 0° and 90°, and preferably about 30°, to the axis of rotation 10 through the grip 4 to a blood suction hose 16 which is connected to the lower end of the channel 14. In this way, the blood outlet suction channel 14 extends either axially to the axis of rotation 10 or obliquely from the top front to the bottom rear away from it. On the flow path between the blood inlet suction channel 12 and the blood outlet suction channel 14, the stream of blood rotates, without reverse flows, in only a single direction of eddy rotation.

The cyclone chamber 8 is elongated upward approximately 5 mm to 15 mm in height by a closed gas space 18 arranged at its top. The gas space has a gas space section 20 that protrudes laterally beyond the cyclone chamber 8. The gas space 18 serves as a storage chamber for temporarily receiving gas bubbles and blood foam so that they have time and space to break down and separate into air and blood. In this way, the blood portion which is drawn off, separated from the rotating stream of blood, with the gas is reduced. The gas space 18 also serves for temporarily receiving blood which may at times rise from the cyclone chamber 8. The cross section of the gas space 18 transverse to the axis of rotation 10 is at least twice as great as the cross section of a gas outlet opening 23.

A gas outlet suction channel 22 extends through the grip 4, parallel to the blood outlet suction channel 14. It is connected via the gas outlet opening 23 in the bottom of the laterally protruding section 20 to the gas space 18. The gas outlet opening 23 is arranged substantially higher, for instance 2 mm to 10 mm higher, than the blood inlet opening 13. A gas removal hose 24 is connected to the gas outlet suction channel 22 at the lower end of the grip 4. The gas suction hose 24 and the blood suction hose 16 are connected separately to a suction pump 28, preferably a peristaltic roller pump, which conveys the blood and the air drawn off on separate paths into a blood reservoir 30. Acting through the blood outlet suction channel 14 and the gas outlet suction channel 22 and then through the gas space 18 and the cyclone chamber 8, the suction pump 28 produces a suction vacuum in the blood inlet suction channel 12 so that blood is drawn into the cyclone chamber 8 through the blood inlet suction channel 12.

The gas space 18 is closed by a cover 34.

A blood suction tube 36 can be detachably inserted into the distal (front) end of the blood inlet suction channel 6. In another embodiment, the blood suction tube 36 may also be in one piece with the body 2 of the device. The front end section of the blood suction tube 36 is bent downward by a downwardly open angle γ of, for instance, 105°. It also has passage openings 39 along it to enable blood to be drawn from the wound site of the patient when an operator holds the body 2 of the device by the grip 4 in a convenient position of his hand. Accordingly, the angle γ of the blood suction tube 36 can be within the range of 90° and 180°.

The grip 4 and, within it, the parallel blood outlet suction channel 14 and gas outlet suction channel 22 all extend obliquely downward to the rear at a downwardly open angle α of between 0° and 90°, and preferably approximately 30°, relative to the cyclone axis of rotation 10. The angles α and γ are so adapted to each other that, upon the drawing off of blood, the apparatus can be held conveniently by the grip and in this connection the gas outlet opening 23 always remains at a higher elevation than the blood inlet opening 13. Therefore, the gas outlet opening 23 is preferably arranged on the side of the chamber facing away from the blood inlet opening 13.

The downwardly open angle δ between the blood outlet suction channel 14 and the gas outlet suction channel 22, on the one hand, and the blood inlet suction channel 12, on the other hand, is, depending on the angles α and β, between about 90° and 180° and preferably, in the preferred embodiment shown, 135°.

In the preferred embodiment, the gas outlet suction channel 22 and its gas suction hose 24 have an inner cross section that is either the same as or different from the blood suction channel 14 and its blood suction hose 16 so that blood and air can be drawn off separately from each other by the same suction pump 28, even if the blood and the air have different volumes of flow.

The conical or funnel shape of the cyclone chamber 8, which narrows in the downward direction from the vicinity of the blood inlet opening 13 to the vicinity of the blood outlet opening 15, assures that the energy of rotation of the stream of blood is maintained without substantial loss from the blood inlet suction channel 12 up to the blood outlet suction channel 14, even if only a slight suction, which acts gently on the blood, is produced at the blood outlet 15 by the suction pump 28.

If the downstream end section of the blood inlet suction channel 12 at the blood inlet opening 13 is directed not only essentially tangentially but also obliquely downward at an angle β of less than 90° into the cyclone chamber 18 and is thus inclined in the direction of the suction in the blood outlet suction channel 14, then even small drop-like amounts of blood are rotated so rapidly by this suction in the cyclone chamber 18 that centrifugal forces are produced which separate blood and air.

Figure 4:
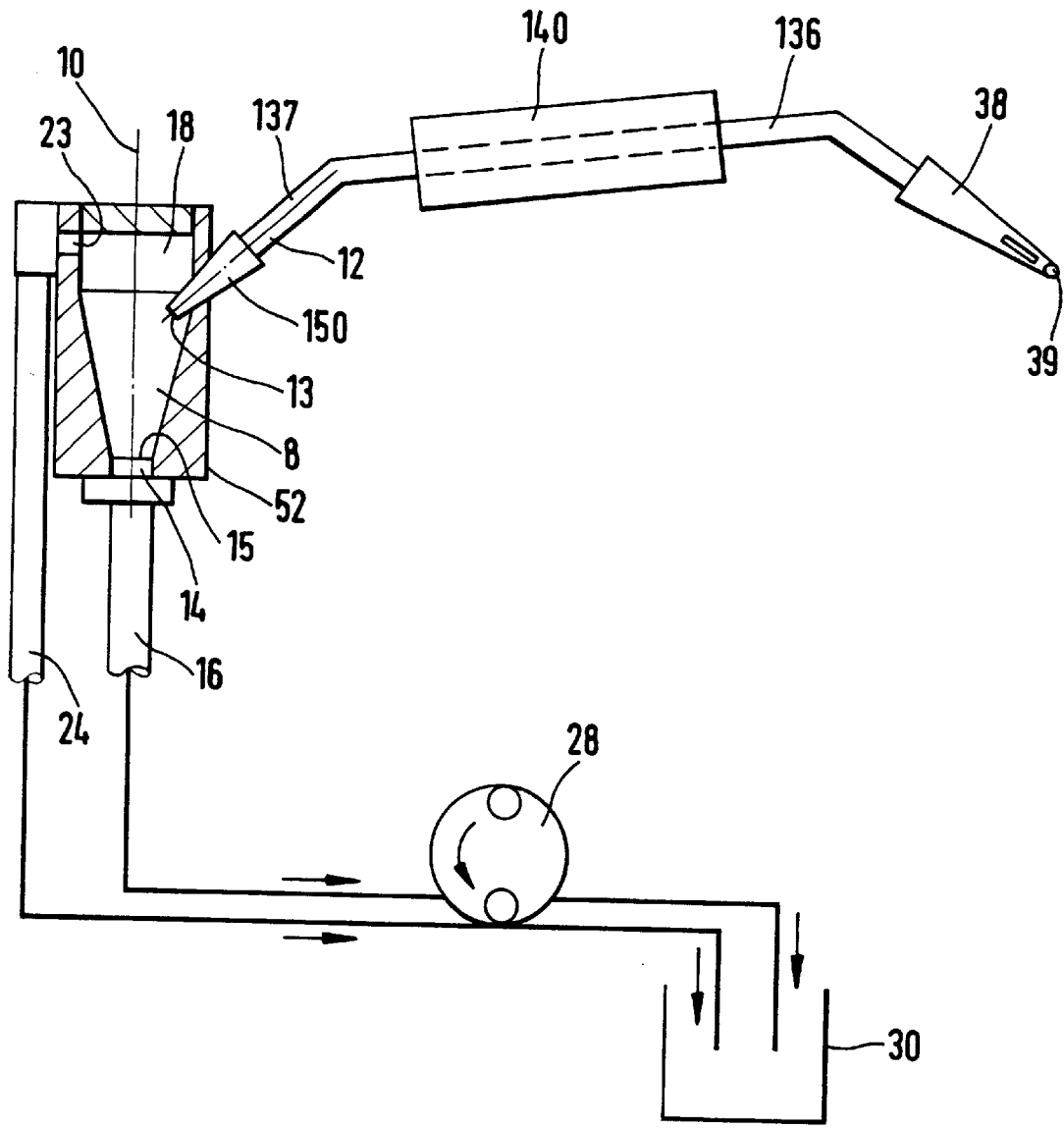
FIG. 4 is a side view, partially in section, of another embodiment of the invention.

In the embodiment of the invention shown in FIG. 4, a commercial blood suction tube 136 having a hand grip part 140 is used. The downstream, rear end section 137 of the blood suction tube 136 forms, directly or by a connecting piece 150, the blood inlet suction channel 12 with the blood inlet opening 13 in the cyclone chamber 8. The cyclone chamber 8 and the upwardly extending gas space 18 which adjoins it at its upper end are formed in a housing 52. The other details which are shown in FIG. 4 are structurally and at least functionally identical to the views of FIGS. 1 to 3 and are provided with the same reference numerals.

Figure 5:
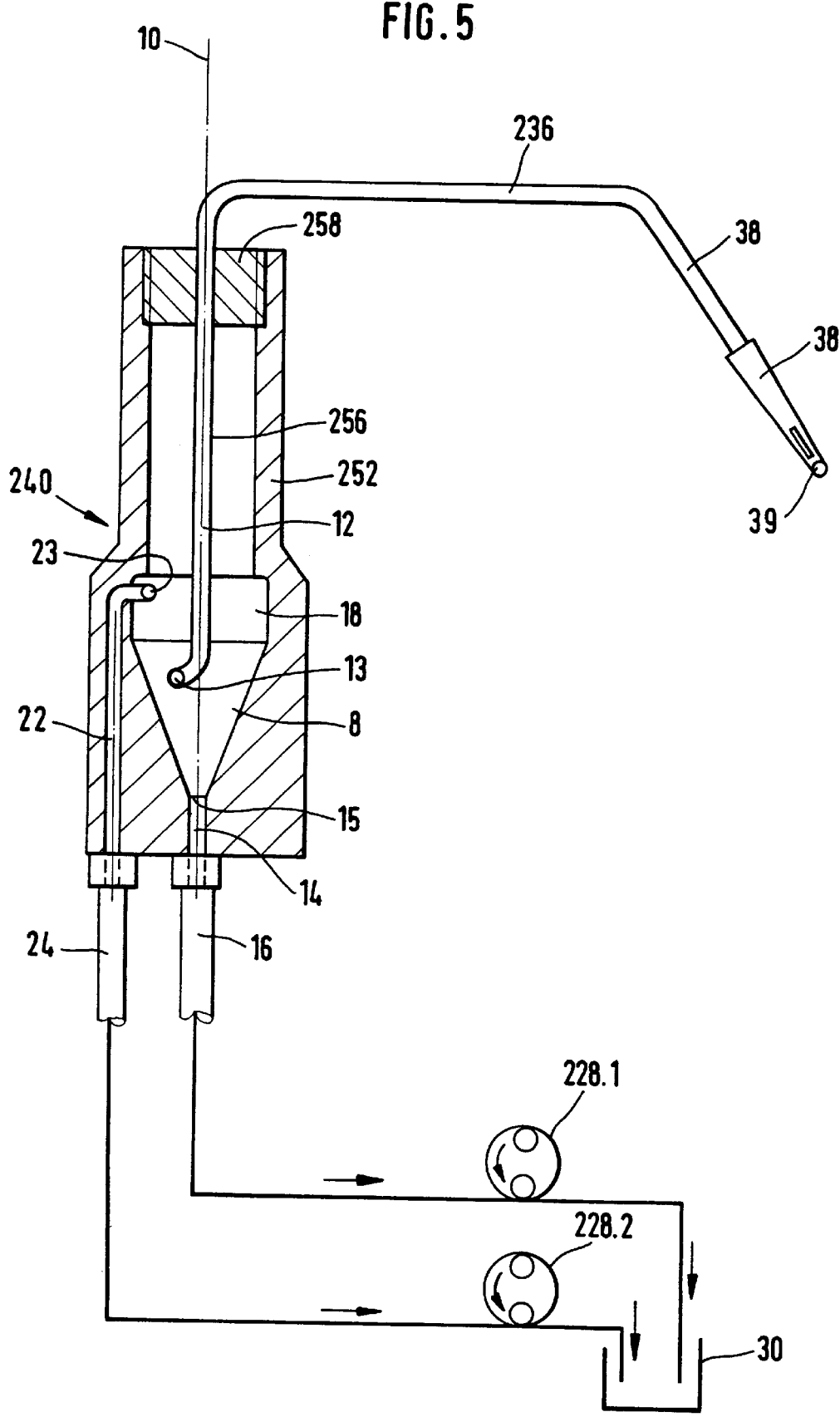
FIG. 5 is a side view, partially in section, of still another embodiment of the invention.

In the further embodiment of the invention shown in FIG. 5, the cyclone chamber 8 and the gas space 18 are formed in a housing 252 which is also developed as a hand grip part 240. This enables the entire device to be carried in one hand. The blood suction tube 236 is provided on its downstream rear end with a length of tube 256 that extends vertically from above and into the housing 252. It forms the blood inlet suction channel 12 and, at its downstream end, it forms the blood inlet opening 13. The gas space 18 is closed at its top by a closure 258 at the upper end of the housing 252. A suction pump 228.1 for the blood and a separate suction pump 228.2 for the gas are provided. But the two pumps can be replaced by a single pump 28 in accordance with FIGS. 1 to 4. The vacuum generated by these pumps produces, through the gas outlet opening 23, the blood outlet opening 15, the cyclone chamber 18 and the blood suction tube 236, a vacuum or suction which draws blood from the wound site of a patient and into openings 39 on the front end of the catheter. The further parts of the embodiment of FIG. 5 are the same as in the embodiment of FIGS. 1 to 3 and are provided with the same reference numerals.

In FIGS. 4 and 5, the blood outlet suction channels 14 are aligned with the vertical axis of rotation 10 of the cyclone chamber 8, which acts as a centrifuge chamber.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A blood suction apparatus for drawing in blood, comprising:
   a non-rotating centrifuge chamber having a substantially vertical axis of rotation and the chamber being shaped for enabling a stream of blood to rotate around the interior of the chamber around the axis of rotation of the chamber, the chamber having an upper end and a lower end;
   a blood inlet suction channel communicating to the upper end of the chamber substantially tangentially to a vertical axis;
   a blood outlet suction channel at the lower end of the chamber; the blood inlet and outlet channels and the chamber being so shaped and placed that a stream of blood is aspirated from the blood inlet suction channel, rotates around the chamber and exits the blood outlet suction channel due to suction applied thereto, wherein the blood is moved radially outwardly by centrifugal force while gas contained in the blood is displaced radially inwardly by the rotating blood;
   an enlarged gas space defined in the apparatus above the blood inlet opening of the blood inlet suction channel and communicating with the chamber, a gas outlet opening communicating in the gas space, a gas outlet suction channel communicating with the gas outlet opening and connectable to a gas suction apparatus, wherein gas in the blood flow may separate in the gas space to be drawn off through the gas outlet suction channel;
   a blood suction tube for sucking in blood and being connected with the blood inlet suction channel.

2. The apparatus of claim 1, wherein the centrifuge chamber has a generally narrowing funnel shape which narrows from about the vicinity of the blood inlet opening down to the vicinity of the blood outlet opening.

3. The apparatus of claim 2, wherein the blood inlet suction channel has a downstream end section at the blood inlet opening and the downstream end section is directed obliquely downwardly into the centrifuge chamber at an angle measured opening toward the top of less than 90° to the axis of rotation.

4. The apparatus of claim 1, wherein the blood inlet suction channel has a downstream end section at the blood inlet opening and the downstream end section is directed obliquely downwardly into the centrifuge chamber at an angle measured opening toward the top of less than 90° to the axis of rotation.

5. The apparatus of claim 1, wherein the apparatus is shaped to be carried in one hand, including a handgrip part thereof.

6. The apparatus of claim 5, wherein the blood inlet suction channel is formed by an end section of the blood suction tube.

7. The apparatus of claim 6, wherein the handgrip is part of the blood suction tube.

8. The apparatus of claim 7, wherein the blood suction tube has a rear end and a front suction tip, the centrifuge chamber is arranged at the rear end of the blood suction tube away from the front tip and the handgrip is arranged between the rear end and front tip of the tube.

9. The apparatus of claim 5, wherein the handgrip part has an upper end and the centrifuge chamber is arranged in the upper end of the handgrip.

10. The apparatus of claim 9, wherein the handgrip is oriented obliquely to the axis of rotation in the centrifuge chamber and obliquely to the blood inlet suction channel.

11. The apparatus of claim 10, wherein the handgrip has a front upper end at the blood inlet suction channel and has a rear bottom end, and the handgrip extends obliquely rearwardly and downwardly from the front upper end to the rear bottom end thereof.

12. The apparatus of claim 5, wherein the handgrip is developed so that both the blood outlet suction channel and the gas outlet suction channel extend alongside each other longitudinally through the handgrip.

13. The apparatus of claim 5, wherein the handgrip comprises a body in which the centrifuge chamber and the gas space are also included.

14. The apparatus of claim 1, wherein the blood outlet suction channel has a different cross-section opening size than the air outlet suction channel.

15. The apparatus of claim 1, further comprising a suction pump with two separated suction paths for defining both a blood suction apparatus and a gas suction apparatus connected respectively to the blood outlet suction channel and the gas outlet suction channel.

* * * * *